United States Patent [19]
Akimoto et al.

[11] Patent Number: 5,981,588
[45] Date of Patent: *Nov. 9, 1999

[54] ω9-UNSATURATED FATTY ACID COMPOSITIONS FOR PREVENTING OR ALLEVIATING MEDICAL SYMPTOMS CAUSED BY DELAYED ALLERGY REACTIONS

[75] Inventors: Kengo Akimoto, Osaka; Hiroshi Kawashima, Takatsuki; Tomohito Hamazaki; Shigeki Sawazaki, both of Toyama, all of Japan

[73] Assignee: Suntory Limited, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/513,084

[22] Filed: Aug. 9, 1995

[30] Foreign Application Priority Data

Aug. 9, 1994 [JP] Japan .................................. 6-187501

[51] Int. Cl.$^6$ .................................................. A61K 31/20
[52] U.S. Cl. ............................................ 514/560; 435/134
[58] Field of Search ............................ 514/560; 435/134

[56] References Cited

U.S. PATENT DOCUMENTS

| | | |
|---|---|---|
| 4,432,906 | 2/1984 | Cohen et al. ..................... 260/410.9 R |
| 4,434,101 | 2/1984 | Cohen et al. ..................... 260/410.9 R |
| 4,681,896 | 7/1987 | Horrobin . |
| 5,130,147 | 7/1992 | Karu .............................................. 426/2 |
| 5,260,336 | 11/1993 | Forse et al. ............................. 514/560 |
| 5,589,508 | 12/1996 | Schlotzer et al. . |

FOREIGN PATENT DOCUMENTS

| | | |
|---|---|---|
| 0 260 655 | 3/1988 | European Pat. Off. . |
| 0 635 266 | 1/1995 | European Pat. Off. . |
| A-62-195346 | 8/1987 | Japan . |
| A-63-072648 | 4/1988 | Japan . |
| A-64-019040 | 1/1989 | Japan . |
| A-64-026532 | 1/1989 | Japan . |
| 6033087 | 2/1994 | Japan . |

OTHER PUBLICATIONS

Michael James et al., "Effect of Dietary Supplementation with n–9 Eicosatrienoic Acid on Leukotriene $B_4$ Synthesis in Rats: A Novel Approach to Inhibition of Eicosanoid Synthesis". *The Journal of Experimental Medicine*, 178(6):2261–2265 (1993).

Lefkowith, et al., "Manipulation of the Acute Inflammatory Response by Dietary Polyunsaturated Fatty Acid Modulation," *The Journal of Immunology*, 145 (Sep. 1990) pp. 1523–1529.

Marone, et al., "An Inhibitor of Lipoxygenase Inhibits Histamine Release from Human Basophils," *Clinical Immunology and Immunopathology*, 17 (1980) pp. 117–122.

Jakschik, et al., "Products Derived from 5,8,11–Eicosatrienoic Acid by the 5–Lipoxygenase–Leukotriene Pathway," *The Journal of Biological Chemistry*, 258 (Nov. 1983) pp. 12797–12800.

Stenson et al, "Leukotriene B Formation by Neutrophils from Essential Fatty Acid–deficient Rats", *The Journal of Biological Chemistry*, 259(19):11784–11789 (1984).

CA 119: 225065, James et al, 1993.

*Primary Examiner*—Rebecca Cook
*Attorney, Agent, or Firm*—Burns, Doane, Swecker & Mathis, L.L.P.

[57] ABSTRACT

A preventive or improving agent for medical symptoms accompanying delayed allergy reactions which contains an ω9-unsaturated fatty acid as an effective component is provided.

9 Claims, No Drawings

ω9-UNSATURATED FATTY ACID COMPOSITIONS FOR PREVENTING OR ALLEVIATING MEDICAL SYMPTOMS CAUSED BY DELAYED ALLERGY REACTIONS

BACKGROUND OF INVENTION

1. Field of Invention

The present invention relates to a preventive or alleviating agent for medical symptoms by delayed allergy reactions, which contains an ω9-unsaturated fatty acid as an effective component, and to a food or drink with a preventive or alleviating effect on medical symptoms by delayed allergy reactions. Specifically, it relates to a preventive or alleviating agent, or a food or drink with a preventive or alleviating effect against medical symptoms by delayed allergy reactions which contains as an effective component at least one selected from the group consisting of 6,9-octadecadienoic acid, 8,11-eicosadienoic acid and 5,8,11-eicosatrienoic acid.

2. Related Art

Allergy reactions are classified into 4 types, types I to IV, based on the antibodies contributing to the reaction, differences in the reaction mechanisms, presence of complement, etc. Of these, type IV allergy reactions differ from the other types of allergy reactions in that antibodies thereto cannot be detected in the blood of individuals in such an allergic state, and it is elicited by lymphocytes. Because at least 12 hours must pass from invasion of the antigen into the allergic individual until appearance of the inflammatory reaction, the type IV allergy reaction is known as "delayed type hypersensitivity".

The T lymphocytes (sensitized T lymphocytes) of individuals in an allergic condition react with the antigen, triggering the T lymphocytes to release lymphokines (macrophage migration inhibitory factor (MIF), macrophage activating factor (MAF), mitogenic factor (MF), skin-reactive factor (SRF), chemotactic factor, neovascularization-accelerating factor, etc.), which function as inflammation mediators, and the biological activity of these lymphokines, together with the direct and indirect effects of locally appearing lymphocytes and other inflammatory cells, give rise to the type IV allergy reaction (delayed allergy reaction).

Delayed allergy reactions include tuberculin type reaction, homograft rejection reaction, cell-dependent type protective reaction, contact dermatitis hypersensitivity reaction, and the like, which are known to be most strongly suppressed by steroidal agents. Consequently, steroidal agents are effective against diseases which are caused by delayed allergy reactions; however, since long-term use of steroidal agents leads to the serious side-effect known as steroid dependence, there are difficulties associated with the termination periods and methods for their administration. It has been strongly desired, therefore, to develop non-steroidal delayed allergy reaction suppressants, which have few side effects.

On the other hand, it has been reported that synthesis of leucotriene $B_4$ is inhibited in the cells of rats raised on feed containing the ω9-unsaturated fatty acid, 5,8,11-cis-eicosatrienoic acid (mead acid) (J. Exp. Med., The Rockefeller University Press, vol.178, Dec. 1993, p.2261–5), although it was not clear whether or not delayed allergy reaction was suppressed.

DISCLOSURE OF THE INVENTION

The present invention, therefore, is aimed at providing an agent which is effective as a preventive or alleviating agent against medical symptoms accompanying delayed allergy reactions, with relatively few side-effects and with applicability to chronic symptoms, as well as a novel food or drink with a preventive or alleviating effect on medical symptoms accompanying delayed allergy reactions.

In order to achieve the above-mentioned object, the present inventors have studied a number of unsaturated fatty acids, and have completed the present invention upon the discovery of ω9-unsaturated fatty acids which have an excellent effect of suppressing delayed allergy reactions and hence are very useful for the prevention and alleviation of medical symptoms by delayed allergy reactions.

The ω9-unsaturated fatty acid which is the effective component according to the present invention is one which has 2 or more double bonds and preferably 18 to 22 carbon atoms, wherein the double bond nearest the methyl end of the fatty acid is between the 9th and 10th carbons counting from the methyl end, and examples thereof include 6,9-octadecadienoic acid, 8,11-eicosadienoic acid and 5,8,11-eicosatrienoic acid etc. These fatty acids may be used alone or in combination.

Because all of the naturally occurring ω9-unsaturated fatty acids are cis-type, cis-type ω9-unsaturated fatty acids are preferably used according to the present invention.

Furthermore, although the ω9-unsaturated fatty acids of the present invention may be used in a form of a free fatty acid, they may also be used in various other forms, for example, pharmaceutically acceptable salt, for example, salts of alkaline metal such as sodium, potassium, lithium or other alkaline metal, salts of other metals such as alkaline earth metal, such as zinc, calcium or magnesium, or in a form of mono-, di- or triglycerides, esters of lower alcohols, phospholipids, glycolipids, amides, or the like, with ethyl esters and triglycerides being particularly preferred. Here, the lower alcohol means monohydric alcohol having 6 or less carbon atoms, specific examples of which are methanol, ethanol, propanol, isopropanol, butanol, pentanol, hexanol etc. These may be used alone or in any combination.

Any source may be used to supply the ω9-unsaturated fatty acid to be used according to the present invention. That is, it may be a fatty acid produced by a microorganism capable of producing ω9-unsaturated fatty acids, animal tissue which is deficient in essential fatty acids or by cultured animal cells which are deficient in essential fatty acids, a fatty acid synthesized by chemical or enzymatic means, or a fatty acid which has been extracted, separated and purified from a natural source, such as animal cartilage.

As microorganisms capable of producing ω9-unsaturated fatty acids, there may be used microorganisms having Δ5 desaturase activity and Δ6 desaturase activity, and having reduced or no Δ12 desaturatse activity, for example described in Japanese Unexamined Patent Publication No. 5-91888, such as *Mortierella alpina* SAM1861 (FERM BP-3590). *Mortierella alpina* SAM 1861 (FERM BP-3590) was deposited on Sep. 30, 1991, with the National Institute of Bioscience and Human Technology Agency of Industrial Science and Technology, 1–3 Higashi 1-chome, Tsukuba-shi, Ibaraki-ken, Japan.

Extraction, separation and purification of the free ω9-unsaturated fatty acids or esters thereof from such microorganisms may be carried out by conventional methods, wherein a fat or oil obtained from microbial cells, for example, by organic solvent extraction with n-hexane or the like or by supercritical carbon dioxide gas extraction, is subjected to hydrolysis to make a mixture of free fatty acids and esterification to make a mixture of fatty acid esters, which is then subjected to urea fractionation, liquid-liquid partition chromatography, column chromatography, etc. to obtain a desired fatty acid such as 6,9-cis-octadecadienoic acid, 8,11-cis-eicosadienoic acid, 5,8,11-cis-eicosatrienoic acid etc. in form of free fatty acid or fatty acid ester, at a purity of 80% or greater. More specifically, the extraction, separation and purification may be carried out by the method described in Japanese Unexamined Patent Publication (Kokai) No. 5-91888.

According to the present invention, not only highly purified fatty acid, but also a mixture of free fatty acids (including free omega 9 series unsaturated fatty acids), a mixture of fatty acid esters (including omega 9 series unsaturated fatty acid esters) or a fat and oil (including omega 9 series unsaturated fatty acids in form of a free fatty acid, mono-, di- or tri-glyceride, phospholipid, glycolipid, or amides) can be used. The fat and oil can be obtained by extracting from cultured microbial cells of microorganisms capable of producing an omega 9 series unsaturated fatty acid according to the above-mentioned method. The mixture of free fatty acids or the mixture of fatty acid esters can be obtained by isolating from the fat and oil according to the above-mentioned method.

The preventive or alleviating agent for medical symptoms caused by delayed allergy reactions according to the present invention may be prepared by combining the effective component of the present invention, an ω9-unsaturated fatty acid, with a commonly used carrier, adjuvant, additive, or the like, and it may be utilized in oral or parenteral form according to the common manner in the field of drugs, topical medicines, cosmetics or foods for sick person, healthy person or infant.

Because the effective component of the present invention, an ω9-unsaturated fatty acid, has an effect of suppressing delayed allergy reactions, it may be applied for the prevention or alleviation of medical symptoms caused by delayed allergy reactions.

Medical symptoms caused by delayed allergy reactions which are the object of the present invention include, for example, tuberculin reaction of tuberculosis allergy, eczema of allergic contact dermatitis, and skin graft rejection reaction, which are skin lesions proven to occur as a result of delayed allergy reactions, while diseases in which delayed allergy reactions are believed to play a part include autoimmune diseases (thyroiditis, encephalitis), infections (for example, cavitation due to tuberculosis), drug allergies (local), contact dermatitis (allergic contact dermatitis) due to allergic antigens (various substances such as chrome and nickel salts and synthetic resins), hepatitis, nephritis, graft rejection reaction, drug rash, lichen planus, erythema induratum Bazin, erythroderma and palmoplantar pustulosis. According to the present invention, alleviation of symptoms is used in a wide sense to also include treatment of the diseases.

When the fatty acids of the present invention are used as a drug, it may be administered in any convenient oral or parenteral form, such as an injection, infusion, powder, granules, tablets, capsules, enteric agent, troches, mixture for internal use, suspension, emulsion, syrup, liquid for external use, fomentations, nasal drop, ear drop, eye drop, inhalant, ointment, lotion, suppository or the like, and any of these may be used independently or in combination, depending on the symptoms.

These preparations may be prepared using known adjuvants commonly used in the field of drug formulation techniques, such as stabilizers, antioxidants, excipients, binders, disintegrators, lubricants, corrective agents, and the like, in addition to the active component. An administration dose varies depending on the purpose of administration and the conditions (sex, age, body weight, etc.) of the patient, but generally, where the fatty acid is orally administered to an adult human, its daily dose is 1 mg to 10 g, and preferably 1 mg to 5g, and more preferably 1 mg to 2g; and for parenteral administration, daily dose is 0.1 mg to 1 g, and preferably 0.1 to 250 mg, and more preferably 0.1 to 10 mg.

The fatty acid which is the effective component of the present invention is known to be biosynthesized by the body in a state of deficiency of essential fatty acids, and its safety is also manifest from the fact that 7-week-old male IRC mice given 2 g/day/kg continuously for 2 weeks (orally) exhibited no abnormal symptoms.

When the fatty acids of the present invention are used in the form of a food or drink it may be the form of any of the above-mentioned preparations, and the recommended amount of the fatty acids of the present invention may be added to a food stuff, particularly a food stuff which originally contains substantially no ω9-unsaturated fatty acid of the present invention, and the food may be processed by a conventional production method. The content of the ω9-unsaturated fatty acid will differ depending on the form of preparation and character of the food, but generally the content is preferred to be 0.001 to 50 wt % with respect to the total weight of the food, though it is not restricted to this range.

Particularly, the ingestion of the ω9-unsaturated fatty acid as a healthy food or functional food is useful for the prevention or alleviation of medical symptoms induced by delayed allergy reactions, and while any of the above-mentioned medicinal preparation forms may be used, other examples are processed forms such as liquid diet foods, semidigested diet foods and component diet foods, and drinkable preparations, which contain the fatty acids of the present invention in combination with, for example, protein (widely used protein sources include milk protein, soybean protein, egg albumin, etc., which have high nutritional value with good amino acid balance, but decomposition products thereof, egg-white oligopeptides, soybean hydrolysates, as well as mixtures of simple amino acids, may also be used), saccharides, fat, trace elements, vitamins, emulsifiers, aromatics, or the like.

A fatty acid of the present invention may also be added to any desired food during the preparation of hospital meals and given to patients in the form of a functional food prepared in situ, under the supervision of a dietician based on a dietary slip from a physician.

A food containing a fatty acid of the present invention used for the purpose of prevention or alleviation of medical symptoms induced by delayed allergy reactions or for maintaining healthy condition is preferably taken orally in an amount in the range of 1 mg/day to 10 g/day, preferably 1 mg/day to 5 g/day, and more preferably 1 mg/day to 2 g/day of the present fatty acid as a general criterium.

The food product may be in the form of a solid, liquid or any other type of preferred food, for example bread, noodles, rice, confectioneries (biscuits, cake, candy, chocolate, Japanese sweets), agricultural food products such as tofu (soybean curd) or derivatives thereof; fermented products such as Japanese sake, medicinal liquor, mirin (sweet sake), vinegar, soybean sauce, bean paste or dressing; stock farm products such as yogurt, ham, bacon, sausage or mayonnaise; aquatic foods such as boiled fish paste, fried fish paste or fish cakes; drinks such as juices, soft drinks, sports drinks, alcoholic drinks or tea; or the like.

EXAMPLES

The present invention will now be explained in fuller detail by way of the following examples.

Example 1

Ten-week-old male BALB/c mice were sensitized with sheep red blood cells (SRBC), and after 2 days they were divided into 3 groups, each given a control diet (90% lipid-free feed+10% lard), an eicosapentaenoic acid (EPA) diet (90% lipid-free feed+8% lard+2% ethyl eicosapentanenoate) or an mead acid (MA) diet (90% lipid-free feed+8% lard+2% ethyl ester of mead acid (90.1% ethyl ester of mead acid, 7.9% ethyl 6,9-cis-octadecadienoate, 1.4% ethyl oleate and 0.6% ethyl arachidate)).

After one week, the volume of the right hind footpad of each mouse was measured with a volume meter, 50 µl of SRBC (20%) was injected into the foodpad, the volume was measured again after 24 hours, and the difference of the volumes was defined as delayed allergy and expressed as a value obtained by dividing the later measurement by the former measurement.

The delayed allergy was roughly the same in the EPA diet group (0.32±0.18) as in the control diet group (0.38±0.18), but in the MA diet group (0.18±0.11) it was significantly suppressed by about 50% ($P<0.05$, t test, Bonferroni correction).

Example 2

| | |
|---|---|
| Gelatin | 70.0% |
| Glycerine | 22.9% |
| Methyl parahydroxybenzoate | 0.15% |
| Propyl parahydroxybenzoate | 0.51% |
| Water | q.s. |
| Total | 100% |

A soft capsule coating having the above composition was filled with ethyl 5,8,11-cis-eicosatrienoate to obtain soft capsules containing 180 mg/capsule.

Example 3

Two grams of β-cyclodextrin was added to 20 ml of a 20% aqueous ethanol solution, and then 100 mg of ethyl 5,8,11-cis-eicosatrienoate was added while stirring with a stirrer and the mixture was incubated at 50° C. for 2 hours. After cooling to room temperature (at 1 hour), it was incubated at 4° C. for 10 hours while stirring was continued. The resulting precipitate was collected by centrifugation, and after washing with n-hexane it was lyophilized to obtain 1.8 g of a cyclodextrin clathrate compound containing ethyl 5,8,11-cis-octadecadienoate. One gram of this powder was mixed uniformly with 10 liters of a fruit juice to prepare a fruit juice containing ethyl 5,8,11-cis-octadecadienoate.

We claim:

1. A method for preventing or alleviating medical symptoms caused by delayed allergy reaction comprising administering to a patient an ω9-unsaturated fatty acid having at least two double bonds in an amount effective for preventing or alleviating medical symptoms caused by delayed allergy reaction.

2. A method for preventing or alleviating medical symptoms according to claim 1, wherein the ω9-unsaturated fatty acid is selected from the group consisting of 6,9-octadecadienoic acid, 8,11-eicosadienoic acid and 5,8,11-eicosatrienoic acid.

3. A method for preventing or alleviating medical symptoms according to claim 1, wherein the medical symptom results from a delayed allergy reaction in a disease selected from the group consisting of autoimmune diseases, infections, drug allergies, contact dermatitis, hepatitis, nephritis, graft rejection reaction, drug rash, lichen planus, erythema induratum Bazin, erythroderma and palmoplantar pustulosis.

4. A method for preventing or alleviating medical symptoms according to claim 3, wherein the medical symptom is contact dermatitis.

5. A method for preventing or alleviating medical symptoms according to claim 1, wherein the ω9-unsaturated fatty acid is administered orally or parenterally.

6. A method for preventing or alleviating medical symptoms according to claim 1, wherein the ω9-unsaturated fatty acid is administered in an amount of between 1 mg and 10 mg per day.

7. A method for preventing or alleviating medical symptoms according to claim 1, wherein the medical symptoms are skin conditions.

8. A method for preventing or alleviating medical symptoms caused by delayed allergy reactions comprising administering to a patient a food or drink which comprises an ω9-unsaturated fatty acid having at least two double bonds in an amount effective for preventing or alleviating medical symptoms caused by delayed allergy reaction.

9. A method according to claim 8, wherein the ω9-unsaturated fatty acid is at least one selected from the group consisting of 6,9-octadecadienoic acid, 8,11-eicosadienoic acid and 5,8,11-eicosatrienoic acid.

* * * * *